United States Patent
Trese et al.

(10) Patent No.: US 6,787,135 B2
(45) Date of Patent: Sep. 7, 2004

(54) MODIFICATION OF VITREAL MATRIX METALLOPROTEINASE ACTIVITY

(75) Inventors: Michael T. Trese, Bloomfield Hills, MI (US); George A. Williams, Bloomfield Hills, MI (US); Michael Hartzer, Rochester Hills, MI (US); Wendelin Dailey, Orion, MI (US)

(73) Assignee: William Beaumont Hospital, Royal Oak, MI (US)

( * ) Notice: Subject to any disclaimer, the term of this patent is extended or adjusted under 35 U.S.C. 154(b) by 55 days.

(21) Appl. No.: 10/096,568

(22) Filed: Mar. 13, 2002

(65) Prior Publication Data
US 2003/0175263 A1 Sep. 18, 2003

(51) Int. Cl.[7] .......................... A61K 38/48; A61M 1/00; A01N 37/18; A61B 3/00; A61B 19/00
(52) U.S. Cl. ..................... 424/94.64; 604/35; 514/2; 351/245; 128/898; 424/94.61; 424/94.62; 424/423
(58) Field of Search ................. 686/107; 604/521.33, 604/35; 137/116.3; 424/94.64, 423, 94.63, 427–424, 94.61, 94.62; 128/898; 514/44, 1–2, 21; 351/245, 423, 450

(56) References Cited

U.S. PATENT DOCUMENTS

| | | | |
|---|---|---|---|
| 4,135,514 A | * 1/1979 | Zaffaroni et al. | ............ 424/428 |
| 5,260,059 A | 11/1993 | Acott et al. | |
| 5,304,118 A | * 4/1994 | Trese et al. | .................. 604/521 |
| 6,083,155 A | 7/2000 | Trese | |
| 6,183,692 B1 | 2/2001 | Trese et al. | |
| 6,207,066 B1 | 3/2001 | Trese et al. | |
| 6,585,972 B2 | * 7/2003 | Peyman | ................... 424/94.64 |
| 2002/0139178 A1 | * 10/2002 | Trese et al. | .................. 128/898 |

OTHER PUBLICATIONS

Trese et al, A new approach to stage 3 Macular holes, American Academy of opthalmology, Apr. 4, 2002.*

* cited by examiner

Primary Examiner—Brian L. Casler
Assistant Examiner—Roz Maiorino
(74) Attorney, Agent, or Firm—Brinks Hofer Gilson & Lione

(57) ABSTRACT

Methods of modifying total MMP activity levels in the vitreous of an eye are provided. In a preferred embodiment, the method results in reduced MMP activity and comprises introducing plasmin into the vitreous of the eye. Enzyme assisted vitrectomy procedures are also provided, and comprise introducing plasmin into the vitreous in an amount sufficient to induce posterior detachment of the vitreous, mechanically detaching the vitreous from the eye, introducing a replacement fluid into the eye, and introducing plasmin into the eye in an amount sufficient to decrease the total MMP activity in vitreous. Considering the purported roles of MMPs in a variety of vitreal pathologies, the present invention provides methods of inhibiting the progression of various disease conditions, including prolifertaive diabetic retinopathy.

18 Claims, No Drawings

MODIFICATION OF VITREAL MATRIX METALLOPROTEINASE ACTIVITY

FIELD OF THE INVENTION

The present invention relates to methods of inhibiting the progression of various pathologies of the vitreous humor that are related to activity of matrix metalloproteinases. More particularly, the invention relates to methods of modifying the total activity of matrix metalloproteinases in the vitreous humor.

BACKGROUND OF THE INVENTION

Matrix metalloproteinases (MMPs) are a group of enzymes responsible for the degradation of extracellular matrix components. The activity of MMPs is dependent on the presence of zinc and is inhibited by the tissue inhibitors of metalloproteinases (TIMPs). Together, the MMPs and TIMPs are believed to play a significant role in a variety of physiological processes, including embryonic development, wound healing, bone growth, tissue remodeling, and vasculogenesis. Furthermore, the MMPs have been implicated in several pathological conditions, such as arthritis, glomerulonephritis, tumor invasion, metastasis, and angiogenesis. (Woesner, J. F. The matrix metalloprotease family. In: Parks, W C and Mechan R P. eds. Matrix Metalloproteinase. London Academic Press; 1998:1–13; Martrisian, L M. The matrix-degrading metalloprotease. Bioessays; 1992, 14:445–463; Krane, S M. The clinical importance of metalloprotease and their inhibitors. Ann NY Acad, Sci, 1994, 732:1–10).

Several MMPs have been identified in human vitreous. (Brown, D., Hamdi H, Bahei S, Keeney M C. Characterization of an endogenous metalloprotease in human vitreous. Curr Eye Res 1994; 13:639–647; Brown D J, Bishop P, Hamdi H, Keeney M C, Cleavage of structural components of mammalian vitreous by endogenous matrix metalloproteainase-2. Curr Eye Res 1996; 15:439–445; Plantner J J, Smine A, Quinn T A. Matrix metalloproteinases and metalloproteinase inhibitors in human interphotoreceptor matrix and vitreous. Curr Eye Res. 1998;17:132–140; De La Paz, M A, Itaoh Y, Toth Ca, Negase H. Matrix metalloproteinase and their inhibitors in human vitreous. Invest Opthalmol Vis Sci 1998;39:1256–1260). While the role of MMPs in the vitreous remains poorly understood, it is believed that these MMPs play a role in a variety of vitreal pathologies, such as proliferative diabetic retinopathy, proliferative vitreoretinopathy, vitreous liquefaction, and age-related macular degeneration. (Brown, D., Hamdi H, Bahei S, Keeney M C. Characterization of an endogenous metalloprotease in human vitreous. Curr Eye Res 1994; 13:639–647; De La Paz, M A, Itaoh Y, Toth Ca, Negase H. Matrix metalloproteinase and their inhibitors in human vitreous. Invest Opthalmol Vis Sci 1998;39:1256–1260; Das, A, McGuire P G, Eriqat C, et al. Human diabetic neovascular membranes contain high levels of urokinase and metalloproteinase enzymes. Invest Ophthalmol Vis Sci 1999;40:809–813; Limb, G A, Miller K, Chignell A H, et al. Metalloproteinase and TIMP-1 in proliferative vitreoretinopathy. Biochem Soc Trans 1997; 25:234S). Furthermore, vitreal MMPs have been identified in the subretinal space and are believed to play a role in non-pathological conditions, such as the normal turnover of components of the interphotoreceptor matrix. (Padgett, L C, Liu G_m, Werb Z, Lavail, M. Matrix metalloprotease-2 and tissue inhibitor of metalloprotease-1 in the retinal pigment epithelium and interphotoreceptor matrix: vectorial secretion and regulation. Exp Eye Res 1997;64:927–938).

Considering the functions of these enzymes, their presence in the vitreous, and their believed roles in a variety of pathological conditions, modification of vitreal MMP activity may provide therapeutic advantages, such as decrease in neovascularization, which is an important step in the establishment of pathological conditions such as proliferative diabetic retinopathy.

SUMMARY OF THE INVENTION

The present invention provides methods of modifying the total activity level of MMPs in the vitreous. Accordingly, the present invention also provides methods of inhibiting the progression of various vitreous pathologies that are related to the activity of MMPs. Methods according to the present invention include introducing plasmin into the vitreous. Plasmin is a non-specific protease best known for its fibrinolytic properties and role in the clotting cascade of blood. Plasmin has been shown to cleave laminin, fibronectin, and other components of the vitreoretinal juncture. (Liotta, L A, Goldfarb, R H, Brundage, R, Siegal, G P, Terranova, V, Garbisa. Effect of plasminogen activator (urokinase), plasmin, and thrombin on glycoprotein and collagenous components of basement membrane. Cancer Res 1981;41:4629–4636; Papp. B Kovacs, T. Lerent I et al. Conditions of formation of the heparinfibronectin-collagen complex and the effect of plasmin. Biochem Biophys Acts 1987;925:241–247.) Indeed, in U.S. Pat. No. 5,304,118, we have shown that plasmin can successfully be used to induce posterior detachment of the vitreous in a vitrectomy procedure. Plasmin is known to activate MMPs, which are capable of degrading vitreous collagen and producing vitreous liquefaction. (Williams G A. Pharmacologic manipulation of the vitreous during pars plana vitrectomy. In: Alfaro III D V & Liggett P E, eds. Vitreoretinal surgery of the injured eye. Philadelphia: Lipponcott-Raven Publishers, 1999; Kliener, D, Stettler-Stevenson, W. Structural biochemistry and activation of matrix metalloproteases. Curr Opin Cell Biol 1993; 5:891–897). Thus, we originally hypothesized that vitreal administration of plasmin would increase activity levels of vitreal MMPs, ultimately leading to liquefaction of the vitreous. Surprisingly, however, we discovered that, at optimized concentrations, the introduction of plasmin into the vitreous greatly reduces total MMP activity in the vitreous.

Accordingly, in one embodiment, a method according to the present invention comprises modifying total MMP activity in the vitreous by introducing plasmin into the vitreous. Preferably, the amount of plasmin utilized is less than one unit. (One unit of plasmin activity is measured by the hydrolysis of a chromogenic substrate S-2251. Friberger, et al. Methods for Determination of Plasmin, Antiplasmin and Plasminogen by Means of Substrate S-2251. Haemostasis 7: 138–145 1978).

The modulation of MMP activity in the vitreous can be used as part of a enzyme assisted vitrectomy procedure in order to provide therapeutic protection following the procedure. In a preferred embodiment of this method, the invention comprises introducing plasmin into the vitreous in an amount sufficient to induce posterior vitreous detachment, mechanically removing the vitreous from the eye, introducing a suitable replacement fluid into the eye, and introducing plasmin into the replacement fluid in an amount sufficient to modify the total MMP activity in the replacement fluid.

While the invention is described in the claims appended hereto, additional understanding of the invention can be

DETAILED DESCRIPTION OF THE PREFERRED EMBODIMENTS OF THE INVENTION

The following description of preferred embodiments provide examples of the present invention. The embodiments discussed herein are merely exemplary in nature, and are not intended to limit the scope of the invention in any manner. Rather, the description of these preferred embodiments and methods serves to enable a person of ordinary skill in the relevant art to make, use and perform the present invention.

The present invention is based on our discovery that plasmin is able to modify the total activity level of MMPs in the vitreous of an eye. Based on time and plasmin levels, the modification can either be an increase or decrease in MMP activity. Prior to this disclosure, plasmin was considered only to be an activator of MMPs, in the eye.

Our initial studies indicated that a brief (5 minutes) plasmin treatment of vitreous at 150 milliUnits/ml produced an increase in total MMP activity as compared to control vitreous that was left untreated. This observation was consistent with prior observations of plasmin acting as an activator of MMPs.

In these studies, vitreous was mechanically removed from normal porcine eyes within 15 minutes of animal death. Vitreous samples were homogenized, centrifuged at 6500-xg for 30 minutes at 4° C. and then stored at 70° C. until used. Vitreous proteins were extracted by addition of an equal volume of extraction solution or a 10% volume of extraction solution to the vitreous prior to centrifugation as previously reported. (Brown D J, Bishop P, Hamdi H, Keeney M C, Cleavage of structural components of mammalian vitreous by endogenous matrix metalloproteainase-2. Curr Eye Res 1996; 15:439–445). Human plasmin was added to vitreous extracts at concentrations ranging from 4 to 500 milliUnits/ml. For MMP activity assays, vitreous samples were treated at a variety of temperatures for a variety of time periods. Temperatures ranged from 4° C. to 37° C. while time periods ranged from 2 minutes to 22 hours. For untreated vitreous control samples, distilled water was introduced into the vitreous as a substitute for the plasmin treatment.

As indicated above, a brief (5 minute) treatment with plasmin at 150 milliUnits/ml produced a slight increase in total MMP activity as compared to controls. Surprisingly, however, a longer treatment period resulted in a decrease in overall MMP activity levels. Treating the vitreous as above for one hour at 37° C. produce a plasmin dose-dependent decease in total MMP activity. Treatment with plasmin at 250 milliUnits/ml of vitreous reduced total MMP activity to about 25% of that in the control. At 500 milliUnits/ml, plasmin treatment decreased total MMP activity to about 17% of the control.

Several individual MMPs comprise the overall group of MMPs present in the vitreous. For example, MMP-1, MMP-2, and MMP-9 are all known to be active in the vitreous. The total MMP activity assays described above, however, measure total MMP activity present in a sample and did not provide any indication as to the contributions of individual MMPs to the total activity. To investigate the effect of plasmin treatment on specific MMPs, zymography was conducted on treated and control samples.

In these experiments, rabbit vitreous samples were collected at various times after plasmin injection and analyzed using zymography. Samples were prepared by the addition of an equal volume of a sample buffer without a reducing agent (10% glycerol, 1M tris-HCl, pH 6.8). Forty ml of sample were loaded onto wells of 10% SDS gels containing 1 mg/ml of gelatin. Electrophoresis was performed using conventional techniques, gels were removed and incubated in 1% Triton X-100 at 37° C. for 30 minutes. The gels were then rinsed with water and incubated at 37° C. for 24 to 72 hours in buffer containing 5 $\mu$M $CaCl_2$, 0.02% $NaN_3$, and 50 mM Tris-HCl, pH 7.4. Lastly, gels were rinsed with water, stained with Coomassie Blue, and destained according to conventional techniques.

Control vitreous samples revealed two major bands at 72 kDa and 65 kDa. These bands correspond to the pro-enzyme and active forms of MMP-2, the predominant MMP in the vitreous, respectively. A variety of vitreous test samples were treated with human plasmin at concentrations ranging from 24 to 440 milliUnits/ml and incubated at 37° C. for 30 minutes. These samples revealed a dose dependent decrease in MMP-2 and MMP-9 in the vitreous.

Interestingly, MMP-1 levels increased with plasmin treatment, while MMP-2 was only visible in non-plasmin treated control samples and in samples treated with relatively low concentrations of plasmin (less than 88 milliUnits/ml).

In vivo experiments revealed the time course of the plasmin treatment related effect in the vitreous. 400 milliUnits (0.4 Units) of human plasma were injected into the vitreous of rabbit eyes. The vitreous samples were then collected at various times after plasmin injection and analyzed using zymography as described above. Both control and test samples removed 5 minutes after plasmin treatment exhibited a band at 65 kDa which corresponds to the active form of MMP-2. This band was not observed in vitreous samples treated in the same way and harvested at later time points, including 60 minutes, 4 hours, 24 hours, 72 hours, and 7 days following plasmin treatment. Thus, the introduction of 400 milliUnits of plasmin into the vitreous reduces MMP-2 levels. Because MMP-2 comprises the predominant component of total MMPs in the vitreous, this reduction in MMP-2 levels likely accounts for the observed decreases in total MMP-2 activity following plasmin treatment.

In some samples collected 72 hours after plasmin treatment, a band corresponding to MMP-9 was observed.

Our previous patent describes a method of performing a vitrectomy on an eye (see U.S. Pat. No. 5,304,118). The method allows for the detachment of the posterior vitreous from the retina by the injection of plasmin into the eye. The method reduces the amount of mechanical action, such as cutting and tearing, used in vitrectomy procedures. Therefore, the method provides a vitrectomy procedure that involves less mechanical stress to the eye as compared to conventional vitrectomy procedures. As taught in the patent, the amount of plasmin needed to effect the posterior detachment of the vitreous is between 1 and 3 units of plasmin. The effects observed in the present invention occur with the introduction of less plasmin into the vitreous. For example, as described above, in vivo treatment of an eye with 0.4 units (400 milliUnits) produced an observable and sustained decrease in total MMP-2 levels and the total MMP activity.

The methods of the present invention have utility in vitreoretinal research as well as clinical settings. For example, enzyme assisted vitrectomy continues to be evaluated as an adjunctive treatment in vitreous surgery. As indicated above, these procedures offer advantages over conventional procedures, such as lower levels of stress to the eye undergoing treatment. The present invention also provides improved enzyme assisted vitrectomy procedures that include a step of introducing plasmin in an amount sufficient to modify total MMP activity. These procedures can be used to inhibit progression of vitreal pathologies that depend on MMP activity, such as neovascularization.

Preferably, an enzyme assisted vitrectomy procedures according to the present invention comprises introducing plasmin into the vitreous of an eye in an amount sufficient to induce posterior detachment of the vitreous. Next, the vitreous is mechanically detached from the retina using conventional techniques. Simultaneously or subsequently, a replacement fluid, such as physiological saline, is introduced into the eye. Lastly, plasmin is introduced into the replacement fluid in an amount sufficient to modify the total MMP activity levels in vitreous. For the posterior detachment of the vitreous, the amount of plasmin introduced is preferably between one and three units. For the modification of the MMP activity levels, the amount of plasmin introduced is preferably less than one unit. Particularly preferable, the amount of plasmin introduced in this step is between about 88 milliUnits and 1 Unit. More preferable, the amount of plasmin introduced in this step is between 88 and 500 milliUnits. More preferable, the amount of plasmin introduced in this step is between about 250 and 500 milliUnits. Most preferable, the amount of plasmin introduced is about 400 milliUnits (0.4 Units).

It will be appreciated that the administration of plasmin to a vitreous of an eye according to the present invention can be accomplished by any suitable means for introducing a composition into an eye, such as direct injection by conventional needle injection, sustained release by a suitable sustained release device, or the like. It will also be appreciated by those skilled in the art that, no matter the method of introduction utilized, the introduction of plasmin into the eye during any step of the method according to the present invention can optionally be accompanied by simultaneous removal of a portion of fluid, such as the aqueous humor or a replacement fluid, in an effort to eliminate excessive intra-ocular pressure.

Also, the plasmin may be introduced as part of a composition that also contains additional components, such as another enzyme, glycoprotein, polysaccharide, antibiotic, pharmaceutically acceptable diluent, adjuvant, and pharmaceutical carrier.

All references cited in this disclosure are hereby incorporated into this disclosure in their entirety, except to any extent to which they contradict any statement or definition made herein.

The foregoing disclosure includes the best mode devised by the inventors for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations, and should be limited only by the spirit and scope of the following claims.

We claim:

1. A method of performing a vitrectomy on an eye and providing post-procedure treatment to said eye, the method comprising:

introducing between 1 and 3 units of plasma into the vitreous humor of said eye;

removing the vitreous humor from said eye;

introducing replacement fluid into said eye; and introducing plasmin into the replacement fluid at a dosage of between about 88 milliUnits and 1 Unit to decrease total matrix metalloproteinase activity in the vitreous humor.

2. The method of claim 1, wherein the introducing comprises injecting.

3. The method of claim 2, wherein the injecting is by needle.

4. The method of claim 1, wherein the introducing is accomplished by a sustained release device.

5. The method of claim 1, wherein the plasmin is contained within a pharmaceutical composition further comprising one or more of another enzyme, a glycoprotein, a polysaccharide, an antibiotic, a pharmaceutically acceptable diluent, a pharmaceutically acceptable adjuvant, and a pharmaceutically acceptable carrier.

6. The method of claim 1, wherein the dosage is between 250 and 500 milliUnits.

7. The method of claim 1, wherein the dosage is an amount sufficient to decrease the activity of MMP-2.

8. The method of claim 1, wherein the replacement fluid is physiological saline.

9. The method of claim 1 wherein the dosage is about 400 milliUnits of plasmin.

10. The method of claim 1 wherein the plasmin is substantially free of a divalent chelator.

11. A method of performing a vitrectomy on an eye and providing post-procedure treatment to the eye, the method comprising:

introducing between about 1 and 3 units of plasma into the vitreous humor of the eye;

removing the vitreous humor from the eye;

introducing replacement fluid into the eye; and introducing plasmin into the replacement fluid at a dosage of between about 88 milliUnits and 1 Unit to decrease total matrix metalloproteinase activity in the vitreous humor, the plasmin being substantially free of a divalent chelator.

12. The method of claim 11 wherein the introducing comprises injecting.

13. The method of claim 12 wherein the injecting is by needle.

14. The method of claim 11 wherein the introducing is accomplished by a sustained release device.

15. The method of claim 11 wherein the plasmin is contained within a pharmaceutical composition further comprising one or more of another enzyme, a glycoprotein, a polysaccharide, an antibiotic, a pharmaceutically acceptable diluent, a pharmaceutically acceptable adjuvant, and a pharmaceutically acceptable carrier.

16. The method of claim 11 wherein the dosage is between 250 and 500 milliUnits.

17. The method of claim 11 wherein the replacement fluid is physiological saline.

18. The method of claim 11 wherein the dosage is about 400 milliUnits of plasmin.

* * * * *